United States Patent [19]

Fredenburgh

[11] Patent Number: 4,911,915

[45] Date of Patent: Mar. 27, 1990

[54] METHOD OF PROCESSING TISSUE SPECIMENS AND DEHYDRANT SOLVENT FOR USE THEREIN

[75] Inventor: Jerry L. Fredenburgh, Plainwell, Mich.

[73] Assignee: Richard-Allan Medical Industries, Richland, Mich.

[21] Appl. No.: 108,136

[22] Filed: Oct. 13, 1987

[51] Int. Cl.$^4$ .............................................. G01N 1/00
[52] U.S. Cl. .......................................... 424/3; 8/94.11; 106/311; 252/364
[58] Field of Search ..................... 8/94.11; 623/1, 2, 3; 424/3; 106/311; 252/364, 380, 381

[56] References Cited

U.S. PATENT DOCUMENTS 4,300,243  11/1981  Baumgartner ..................... 623/15
4,383,832  5/1983  Fraefel et al. ...................... 8/94.11

Primary Examiner—Paul Lieberman
Assistant Examiner—John F. McNally
Attorney, Agent, or Firm—Gordon W. Hueschen

[57] ABSTRACT

A liquid dehydrating agent suitable for treating histological and cytological tissue in the processing thereof for microscopic examination, consisting essentially of a blend of between 30 and 45 percent by volume of methyl alcohol and between 70 and 55 percent by volume of isopropyl alcohol, the total constituting 100 percent, preferably wherein the amount of isopropyl alcohol is about 60 percent and the amount of methyl alcohol is about 40 percent by volume, and a method of treating histological or cytological tissue to dehydrate the same after fixation thereof, comprising immersing the tissue in such a liquid dehydrating agent, as well as a method of treating histological or cytological tissue after preservation or fixation thereof to dehydrate the same, comprising the step of immersing the tissue in such a liquid dehydrating agent and water, and repeating the procedure with successively diminishing amounts of water, and a method of hydrating histological or cytological tissue comprising the step of subjecting the tissue to a mixture of water and such a liquid dehydrating agent preferably by repeating the step with successively increasing amounts of water, staining the hydrated tissue, and then dehydrating the stained tissue by subjecting it to the same dehydrating agent, are disclosed.

8 Claims, No Drawings

METHOD OF PROCESSING TISSUE SPECIMENS AND DEHYDRANT SOLVENT FOR USE THEREIN

BACKGROUND OF THE INVENTION

1. Field of Invention

A novel dehydrating agent useful in the processing of histological or cytological samples to dehydrate the same, and in the hydration of tissue samples affixed to a microscopic slide for purposes of hydrating the same before staining and then dehydrating the same after staining.

2. Prior Art

Historically, ethyl alcohol has been used as the liquid dehydrant of choice for treating tissue for histological and cytological examination, both in the processing and staining of tissue specimens. Other liquid dehydrating agents have been proposed. Advantages have been claimed for some of them, but the liquid dehydrant of choice remains ethyl alcohol. Isopropyl alcohol and methyl alcohol alone have not been satisfactory, and neither have more complex liquid dehydrating agents of the same type which have been proposed for the same purpose over the years. A representative U.S. Patent is 2,684,925 (the disclosure of which is incorporated herein by reference) issued July 27, 1954, by Ferrari, which outlines the procedure employed and proposes a new liquid dehydrant comprising as essential ingredients diethylene glycol monoethyl ether acetate and a minor proportion of isopropanol. In acquainting myself with the prior art, the closest patents turned up were 2,150,757, 3,389,052, 3,546,334, 3,961,097, 3,995,022, 4,199,558, 4,221,823, 4,300,243, 4,545,831, and 4,656,047, the search having been conducted in Class 34, Subclass 9; Class 252, Subclasses 194, 364, and 408.1; 424, Subclass 3; and 427, Subclass 2, but these are devoid of any suggestion of the present invention. Although the prior art is replete with suggestions of varying procedure and varying solvents which may be employed for preserving tissue and so on, none of these have really been satisfactory in practice and ethyl alcohol or ethanol continues as the dehydrating solvent of choice despite the fact that it is a controlled substance and therefore subject to nearly unbearable regulation. Suggestions that just any lower alcohol is suitable are totally unfounded in practice, as will be shown hereinafter. Moreover, there simply have been no suitable economic and practical substitutes for ethyl alcohol as a dehydrant in the processing and staining of tissue specimens for histological and cytological examination, up to the time of the present invention. Now, however, it has been possible to provide a suitable substitute for ethyl alcohol which is equally acceptable and in some ways in practice, which provides characteristics which are at least equal to those of ethyl alcohol and in superior thereto when used for the intended purpose as a liquid dehydrating agent, and which moreover is not subject to the burdensome regulation imposed upon controlled substances. It is therefore apparent that a long-felt need of the art here involved has now been fulfilled by provision of the composition and method of the present invention.

OBJECTS OF THE INVENTION

It is an object or the present invention to provide a liquid dehydrating agent which performs as well as ethyl alcohol in tissue processing and in routine hematoxylin and eosin staining of tissue specimens. It is a further object to provide such a liquid dehydrating agent which is not a controlled substance requiring burdensome record keeping, but which is rather an inexpensive alternative to the previous liquid dehydrant of choice, namely, ethyl alcohol. An additional object of the invention is to provide such a liquid dehydrant composition consisting essentially of between about 30 and 45 percent by volume of methanol and between about 55 and 70 percent of isopropanol, the total being 100 percent, and especially such composition consisting essentially of about 60 percent isopropanol by volume and 40 percent methanol by volume. A still further object of the invention is a provision of a method of treating histological or cytological tissue for dehydration of the same after fixation thereof with such a liquid dehydrating agent, and a still additional object is the provision of a method for hydrating slide-mounted tissue employing such a liquid dehydrating agent in a hydrating step, and thereafter employing such a liquid dehydrating agent of the invention in the dehydration of such a hydrated slide-mounted tissue specimen after staining of the same. Additional objects of the invention will become apparent hereinafter, and still others will be apparent to one skilled in the art.

BRIEF DESCRIPTION OF THE INVENTION

The invention comprises the aforesaid blend or mixture of methyl alcohol and isopropyl alcohol in the range of about 30 percent to 45 percent by volume of methanol and 70 to 55 percent by volume of isopropanol, the total being 100 percent, and especially such blend or mixture consisting essentially of about 40 percent of methanol and 60 percent of isopropanol. Hereinafter this blend or mixture is sometimes referred to as Agent X or AgtX. The invention also comprises a method of employing such liquid dehydrating agent for dehydration of histological or cytological tissue by immersing the said tissue after preservation of fixation thereof in such a liquid dehydrating agent according to the usual practice and skill of the art, and the invention further comprises the hydration of a slide-mounted tissue specimen employing a liquid dehydrating agent according to the present invention along with a mixture of water, preferably with increasing amounts of water being employed in successive hydration steps, staining of the slide-mounted specimen in its hydrated state, and then dehydrating the same using the special liquid dehydrating agent of the present invention, all of which except for the employment of the particular and special liquid dehydrating agent of the present invention is accomplished or effected according to the normal practice and procedure of the prior art. As already pointed out, the hydration of the slide-mounted specimen is ordinarily and preferably carried out in a succession of steps employing the liquid dehydrating agent of the present invention and water using increasing amounts of water prior to the staining step, whereafter dehydration is effected using the dehydrating agent of the present invention, whereas in the dehydration of histological or cytological tissue the procedure ordinarily and preferably employed is to utilize a liquid dehydrating agent of the present invention together with water but using diminishing amounts of water in a succession of steps ultimately resulting in the desired degree of dehydration of the tissue specimen.

The blend of mixture of solvents constituting the liquid dehydrating agent of the present invention does not suffer from the disadvantages of the individual ingredients or components thereof, namely, methanol and isopropanol, which suffer from serious disadvantages in both tissue processing procedure and in staining of tissue samples and, in view thereof, the characteristics of the liquid dehydrating agent of the present invention must be considered to be not only advantageous but also unpredictable. Accordingly the "subject matter as a whole" must be considered to be unobvious.

SUMMARY OF THE INVENTION

The invention, then, comprises the following inter alia:

A liquid dehydrating agent suitable for treating histological and cytological tissue in the processing thereof for microscopic examination, consisting essentially of a blend of between about 30 and 45 percent by volume of methyl alcohol and between about 70 and 55 percent by volume of isopropyl alcohol, the total constituting 100 percent; such a liquid dehydrating agent wherein the amount of isopropyl alcohol is about 60 percent by volume and the amount of methyl alcohol is about 40 percent by volume; the method of treating histological or cytological tissue to dehydrate the same after fixation thereof, comprising immersing the tissue in a liquid dehydrating agent consisting essentially of such liquid dehydrating agent; the method of treating histological or cytological tissue after preservation or fixation thereof to dehydrate the same, comprising the step of immersing the tissue in a liquid dehydrating agent consisting essentially of such a liquid dehydrating agent and water and preferably repeating the procedure with successively diminishing amounts of water; and finally the method of hydrating histological or cytological tissue mounted on a microscopic slide comprising the step of subjecting the tissue to a mixture of water and such a liquid dehydrating agent and preferably repeating the step with successively increasing amounts of water, staining the hydrated tissue, and then dehydrating the stained tissue by subjecting it to such a dehydrating agent.

Overview of Tissue Processing

The primary concern in tissue processing is the production of a high quality slide so the pathologist can make an accurate diagnosis. Therefore, all stage of tissue processing--beginning with transporting the tissue to the lab and ending with cover slipping -- must be reliable, consistent, and of the highest quality.

Transportation: Tissue processing begins with the clinician surgically removing a tissue specimen from the patient. The tissue is placed in a container (often containing a fixative) and transported to the lab. At this stage, the tissue is called gross tissue.

Fixation: Fixation is the most important step in tissue processing. Chemical reagents called fixatives are used to preserve tissue components in a lifelike manner. Formaldehyde is the most common fixative in the histology lab. It is generally used as a 10% v/v solution in water, also called formalin. A buffer may be added to the 10% formalin solution to prevent tissue artifact or formalin pigmentation.

Decalcification: When calcium salts are present in tissue, the tissue is called calcified. Before calcified tissue can be sectioned by a microtome knife, the calcium salts must be removed, or decalcified. The preferred method of decalcification uses an acid decalcifier combined with a fixative to allow fixation and decalcification to occur simultaneously.

Grossing: The tissue received in the fixative-filled container is examined by the pathologist. Three to five millimeter sections from suspicious areas of the tissue sample are placed in vented, plastic cassettes to be processed.

Tissue Processing: The cassettes containing the tissue are placed into a tissue processor. Here, they are subjected to a series of chemical reagents. Upon completion of the process, the tissue will have been fixed, dehydrated, cleared and infiltrated with paraffin.

There are two types of tissue processors--open processors and closed processors. The open processor moves a basket of tissue-filled cassettes through twelve pre-programmed stations of chemical reagents. The closed processor has a stationary chamber in which the tissue-filed cassettes are placed. Vacuum and/or heat may be applied to the chamber to hasten tissue processing. Chemical reagents enter and exit this chamber in a pre-programmed sequence. Note: The next four steps describe the sequence of tissue processing.

Fixation: The first two stations on the tissue processor generally contain the fixative. This continues the fixation process that was begun during transportation. The time duration in these two stations may range from one hour to six hours.

Dehydration: The next six stations on the tissue processor generally contain the dehydrants. Water is progressively removed from the tissue by using dehydrants graded to an anhydrous state. This allows for minimal tissue shrinkage and the tissue is neither too dry or too soft.

Clearing: Two stations of clearing reagents are commonly used on tissue processors. The clearing reagent is necessary due to the incompatibility of the dehydrant with the infiltrating medium (usually paraffin).

Infiltration: The final two to four stations on the tissue processor contain the infiltrating medium (paraffin). The infiltrating medium provides cellular support for cutting tissue sections.

Embedding: After tissues are infiltrated, they are removed from the tissue processor and taken to the embedding station. Here the tissue is placed in molten embedding medium (paraffin) and formed into blocks. Blocks are then cooled on a coldplate or placed on ice.

Microtomy (cutting): A chilled block is then secured on a microtome. This instrument is used for cutting a tissue section into three to five micron sections. A ribbon is formed by the joining of the individual sections as they are cut.

Water Bath: The ribbons are then floated on a heated water bath (46°-50° C.). This process flattens the tissue section and removes wrinkles, Each slide is dipped into the water to pick up an individual section of the ribbon. Sometimes gelatin or albumen is added to the water bath to help the tissue adhere to the slide.

Heating: The slide with the tissue adhered to its is then heated or baked in an oven. This flattens the section on the slide, helping to eliminate wrinkles. In addition, it helps the section adhere to the slide and helps remove excess paraffin.

Staining: Staining gives color to the tissue nucleus and cytoplasm so that microscopic study can more readily take place. Staining can either be done in an automatic stainer or manually. When manual staining is performed, staining dishes filled with reagents are set up in a staining sequence. A stationary rack holding 20-30 slides is placed in each staining dish for a specified period of time. The rack is lifted by hand from one dish to the next.

Clearing reagents being the staining process. They eliminate any traces of paraffin left in the tissue. Next come dehydrants--which change the tissue to a hydrated state. The slide is then rinsed with distilled (or deionized) water before it is moved to the hematoxylin stain.

Hematoxylin is used to stain the nucleus of the cell from blue to purple. There are two types of hematoxylin: progressive and regressive. Progressive hematoxylin stains the nuclei *to the desired color intensity;* regressive hematoxylin stains the nuclei *beyond the desired color intensity.* (In other words, it overstains the nuclei).

When regressive hematoxylin is used, the excess stain is removed by dipping the slide in an acid alcohol—a process called differentiation.

The slides are then exposed to clarifier to remove the background staining caused by excess tissue adhesive in the water bath.

Bluing reagent is used next to enhance the color of the nuclei; this is sometimes referred to as bluing the nuclei. Bluing reagent changes the color of the hematoxylin from reddish brown to a crisp blue.

Eosin is the next staining station. It is used to stain the cytoplasm different intensities of pink, depending on the time in the stain. The staining of the finished slide will have sharp contrast between the blue of nuclei and the red tones of the cytoplasm.

Cover Slipping: After both hematoxylin and eosin are used, the slide once again passes through the sequence of reagents. The stained slide is put first in dehydrants and then in clearing reagents. The dehydrant removes the excess water while the clearant eliminates the alcohol left from the dehydrant. The clearant is important because the dehydrant is not compatible with the mounting medium.

Next, mounting medium is used to affix the cover glass to the slide. The cover glass protects the tissue section.

The pathologist then studies the slide to make a tissue diagnosis.

| BASIC STEPS IN TISSUE PROCESSING | | |
|---|---|---|
| Procedure | Purpose | Importance |
| Transportation | Placing the tissue specimens in containers and moving them to the histology lab. | To begin fixation process and prevent autolysis and putrefaction. |
| Fixation | Preserving the tissue in a life-like manner by placing it in formalin. | To preserve the tissue properly so subsequent stages of tissue processing will be correct. |
| Decalcification | Removal of calcium salts from bone or other calcified tissue. | To prevent tissue distortions and to allow cutting with the microtome knife. |
| Grossing | Cutting the tissue into specified sample sections and placing these specimens in cassettes for continued processing. | To cut the appropriate sample section. |
| Tissue Processing | Fixation (preserving the tissue), dehydrating (removing the water), clearing (removing the alcohol), and infiltrating the tissue with paraffin. All steps are done on a machine called a tissue processor. | To prepare the tissue so that a thin section can be cut for microscopic examination. |
| Embedding | Filling the entire cassette with paraffin to make a block with the tissue in it. | To support the tissue for easier handling and cutting. |
| Microtomy (Cutting) | Cutting the paraffin block into ribbon-like slices so a thin section can be placed on the slide. | To prepare a thin section of the tissue for study. |
| Water Bath | Floating the thin sections on water to flatten the tissue and remove wrinkles. Gelatin or albumen may be added to the water to promote adherence of the tissue to the slide. A slide is dipped into the water to pick up a single section. | To flatten the section and promote adherence to the slide. |
| Heating | Heating the slide to cause the section to adhere to it. | To prevent displacement of the section. |
| Staining | Coloring the nuclei and cytoplasm of the tissue to provide distinctive features easily studied under a microscope. | To make diagnosis possible. |
| Cover Slipping | Affixing the cover glass to the slide with mounting medium to protect the tissue section. | To complete final preparations for a readable slide which can be stored. |

DETAILED DESCRIPTION OF THE INVENTION

Tissue Processing: Present State-of-the-Art

A known process in the field of histology is referred to as tissue processing. Tissue processing is traditionally done by a machine which subjects tissue specimens to a series of chemical reagents. Upon completion of the process, the tissue will have been fixed, dehydrated, cleared, and infiltrated with paraffin.

Tissues that are to be examined microscopically must be cut into thin sections three to five microns in thinness. Fresh and/or fixed tissue specimens are not firm and cohesive enough to allow for microtome sectioning of three to five microns. To achieve thin section, it is necessary to infiltrate the tissue specimen with a supporting medium to render cellular stability, thus holding the cells and intracellular structures in their proper relationship to one another.

The infiltrate used to render support to tissue specimen is a paraffin-based product. In order to infiltrate the tissue specimen, it is necessary to displace the aqueous fixing fluid and any water remaining in the tissue with a fluid miscible with paraffin. Most water-miscible fluids are not miscible with paraffin; it is necessary to dehydrate the tissue with a water-miscible fluid and then replace the dehydrating reagent with a paraffin solvent which is miscible with both the dehydrant and paraffin infiltrate. This solvent is referred to as a clearing reagent.

The process of removing water from tissue is called dehydration. The said invention deals with this part of tissue processing.

As clearing reagents are ordinarily employed xylene, toluene, branched-chain aliphatics (e.g., isoparaffinic oils) such as Clear-Rite 3 TM from Richard-Allan Industries, Richland, Michigan, and the like, all as is well known in the art.

Tissue Processing Advantages Using the Invention

Traditionally, ethyl alcohol has been the dehydrating reagent of choice because of its versatility of use in tissue processing and staining (see Staining). Other alcohols have made very little progress in their introduction into the lab, but denatured ethyl, isopropyl and methyl alcohol have been used in some cases.* The period of immersion of the tissue specimen in various alcohols and their various strengths will affect the hardness of the tissue specimen. Longer duration in higher percentages (95–100%) ethyl, isopropyl, and methyl alcohol will cause excessive hardening, making the tissue specimen difficult or impossible to cut. Heat and vacuum hasten the process. Alcoholic dehydrants have a hardening effect, which is good to a certain point and is of considerable importance.
*But all have serious disadvantages, as noted herein.

AgtX was developed to perform as ethyl alcohol does in tissue processing and staining (see Staining). AgtX and ethyl alcohol are miscible with all proportions of water and clearing reagents (xylene, other cyclic organic solvents, branched chain aliphatic and D-limonene complexes). AgtX, like ethyl alcohol, can be used as a dehydrant in tissue processing with or without heat and vacuum. AgtX has shown an advantage over ethyl alcohol in not rendering small biopsies as hard, thus facilitating thin sectioning. AgtX and ethyl alcohol are both good lipid extractors and are miscible with all clearing reagents used in tissue processing. AgtX, as ethyl alcohol, shows little shrinkage of tissue specimens when used as a graded tissue dehydrant.

Ethyl alcohol is a controlled substance requiring record keeping by the end user. AgtX is not a controlled substance and requires no record keeping. Isopropyl alcohol is sometimes substituted for ethyl alcohol in tissue processing. Isopropyl alcohol causes the tissue to be overly hardened in processing and cannot be used in staining (see Staining). AgtX is a more gentle dehydrating agent which causes less hardening than isopropyl alcohol. Methyl alcohol does not harden tissue as rapidly as ethyl or isopropyl alcohols, but has three disadvantages:

1. Absolute methyl alcohol cannot be uses in most closed processors.
2. Methyl alcohol is not a universal dehydrant (i.e., can be used for tissue processing only, not staining. (see Staining).
3. Methyl alcohol is not miscible with branched chain aliphatic and D-limonene, two commonly used clearing reagents.

AgtX is a universal dehydrant that can be used in closed and open processors, and is miscible with branch-chain aliphatic and D-limonene clearing reagents.

Staining of Histological Tissue Sections: State of the Art

A known process in the field of Histology is referred to as staining. Staining can either be done with an automatic stainer or manually. Automatic staining and manual staining is accomplished by the movement of the tissue section on microscope slides to and from specific reagents.

Intracellular structures and cell constituents are usually transparent, making them indistinguishable from one another. Biological stains are used to identify and differentiate call constituents and intracellular substance for microscopic study of their relationship. Traditionally, hematoxylin and eosin-y are two biological stains which are used to show cell relationships; special stains relate to biological stains used to identify more specific structures or intracellular substance from one another.

Tissue specimens that have been subjected to tissue processing (see Tissue Processing) and thin-sectioning, are placed on microscope slides and are now ready for staining. The first step of staining involves the removal of the infiltrate and surrounding paraffin from the tissue section. This stage of staining is referred to as deparaffinization.

Deparaffinization is achieved by the use of two or three successive clearing reagents which are paraffin solvents. After deparaffinization, the sections are hydrated to water by a gradual process utilizing graded dehydrant (ethanol)*. The hydration process allows the sections to be stained with aqueous and/or alcoholic-soluble biological dyes. After the application of biological dyes, the tissue sections are dehydrated with successive changes of graded dehydrant (ethanol)*. When dehydration is complete, the tissue sections are passed through several successive clearing reagents which allow for coverslipping. The dehyrating reagent must be miscible with aqueous solutions and clearing reagents.
*In this invention, replaced by Agent X.

Coverslipping is achieved by attaching a thin piece of glass (cover glass) over the tissue section on the microscope slide. The cover glass is attached to the microscope slide with a glue-like reagent called mounting medium. Cover slipping preserves the stained tissue section and allows for subsequent handling and microscopic examination.

Staining Advantages Using the Invention

Traditionally ethyl alcohol has been the dehydrant of choice for hydrating and dehydrating tissue sections during staining. has similar characteristics of ethyl alcohol, i.e.:

(1) Agent X is miscible with water and all clearing reagents.

(2) Agent X is a good dye solvent.

(3) Agent X does not rapidly extract eosin-y and most other biological dyes from tissue sections when used as a dehydrant during staining.

AgtX was designed to act as ethyl alcohol does during staining. The major advantage of AgtX over ethyl alcohol is that AgtX is not a controlled substance, which eliminates the necessity of record keeping and reduces the cost of the product in many cases.

Isopropyl alcohol is sometimes used during staining for hydration and dehydration, but has the disadvantage of being a poor dye solvent. Dyes have very little solubility in isopropyl alcohol and several changes of the dehydrant must be used after the cytoplasmic staining of hematoxylin and eosin-y to achieve the proper contrast.

Methyl alcohol is the least expensive of the alcohols, but because of its great solvent characteristics it cannot generally be used as a dehydrant during staining. Methyl alcohol also is not miscible with D-limonene and branched chain aliphatic clearing reagents.

The following Examples are given to illustrate the present invention, but are not to be construed as limiting.

SAMPLE TISSUE PROCESSING SCHEDULE

| EXAMPLE A STN | SOLUTION | TIME |
|---|---|---|
| 1 | Fixative | hold |
| 2 | Fixative | 1 hour |
| 3 | 80% Dehydrant | 1 hour |
| 4 | 95% Dehydrant | 1 hour |
| 5 | 95% Dehydrant | 1 hour |
| 6 | 100% Dehydrant | 1 hour |
| 7 | 100% Dehydrant | 1 hour |
| 8 | 100% Dehydrant | 1 hour |
| 9 | Clearing Reagent | 1 hour |
| 10 | Clearing Reagent | 1 hour |
| 11 | Paraffin | 1 hour |
| 12 | Paraffin | 1 hour |

% of dehydrant refers to dehydrant diluted with water. EX: 80% Dehydrant = 20% Water and 80% Dehydrant (v/v).
Ethyl alcohol or Agent X used as dehydrant produces a well-processed tissue specimen.
Isopropyl alcohol produces a dry or over-processed tissue specimen.
Methyl alcohol produces a well-processed tissue specimen but can not be used when a D-limonene or branched-chain aliphatic is used as clearing reagent because they are immiscible with methyl alcohol.

SAMPLE STAINING SCHEDULE USING HEMATOXYLIN AND EOSIN

| EXAMPLE B STN | SOLUTION | TIME |
|---|---|---|
| 1 | Clearing Reagent | 3 minutes |
| 2 | Clearing Reagent | 3 minutes |
| 3 | Clearing Reagent | 3 minutes |
| 4 | 100% Dehydrant | 4 dips to 1 minute |
| 5 | 100% Dehydrant | 4 dips to 1 minute |
| 6 | 100% Dehydrant | 4 dips to 1 minute |
| 7 | 95% Dehydrant | 4 dips to 1 minute |
| 8 | Rinse in running tap water | 30 seconds to 1 minute |
| 9 | Distilled water rinse | rinse |
| 10 | Hematoxylin | .5 minutes to 15 minutes |
| 11 | Running water | 30 seconds to 1 minute |
| 12 | Acid rinse | 4 dips to 1 minute |
| 13 | Rinse in running tap water | 1 to 5 minutes |
| 14 | Bluing Reagent | 4 dips to 1 minute |
| 15 | Rinse in running tap water | 1 to 5 minutes |
| 16 | Dehydrant rinse | 4 dips to 1 minute |
| 17 | Eosin-y | 3 dips to 2.5 minutes |
| 18 | 100% Dehydrant | 4 dips to 1 minute |
| 19 | 100% Dehydrant | 4 dips to 1 minute |
| 20 | 100% Dehydrant | 4 dips to 1 minute |
| 21 | Clearing Reagent | 1 minute |
| 22 | Clearing Reagent | 1 minute |
| 23 | Clearing Reagent | 1 minute |

% dehydrant refers to dehydrant diluted with water. EX: 80% Dehydrant = 20% Water and 80% Dehydrant (v/v).
Ethyl alcohol or Agent X used as dehydrant during staining produces a well-stained tissue specimen.
Isopropyl alcohol used as dehydrant during staining produces an unsatisfactory darker Eosin-y stain than ethyl alcohol or Agent X.
Methyl alcohol used as dehydrant during staining produces no or little Eosin-y staining.

In conclusion, from the foregoing, it is apparent that the present invention provides a novel liquid dehydrating agent suitable for use in the treatment and preparation of histological and cytological tissue specimens, consisting essentially of between about 30 and 45 percent by volume of methyl alcohol and 70 to 55 percent by volume of isopropyl alcohol, the total being 100 percent, and preferably about 60 percent of isopropyl alcohol and 40 percent of methyl alcohol by volume, as well as a novel method for the dehydration of tissue specimens and the hydration of slide-mounted tissue specimens for staining, as well as for the dehydration of such hydrated and stained slide-mounted tissue specimens, all having the foregoing enumerate characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

I claim:

1. The method of treating histological or cytological tissue to dehydrate the same after fixation thereof, comprising immersing the tissue in a liquid dehydrating agent consisting essentially of a liquid dehydrating agent consisting essentially of a blend of between about 30 and 45 percent by volume of methyl alcohol and between about 70 and 55 percent by volume of isopropyl alcohol, the total constituting 100 percent.

2. The method of claim 1 of treating histological or cytological tissue to dehydrate the same after fixation thereof, comprising immersing the tissue in a liquid dehydrating agent consisting essentially of a liquid dehydrating agent wherein the amount of isopropyl alcohol is about 60 percent by volume and the amount of methyl alcohol is about 40 percent by volume.

3. The method of treating histological or cytological tissue after preservation or fixation thereof to dehydrate the same, comprising the step of immersing the tissue in a liquid dehydrating agent consisting essentially of a blend of between about 30 and 45 percent by volume of methyl alcohol and between about 70 and 55 percent by volume of isopropyl alcohol, the total constituting 100 percent, and water, and repeating the procedure with successively diminishing amounts of water.

4. The method of claim 3 of treating histological or cytological tissue after preservation or fixation thereof to dehydrate the same, comprising the step of immersing the tissue in a liquid dehydrating agent consisting essentially of a liquid dehydrating agent wherein the amount of isopropyl alcohol is about 60 percent by volume and the amount of methyl alcohol is about 40 percent by volume, and water, and repeating the procedure with successively diminishing amounts of water.

5. The method of hydrating histological or cytological tissue comprising the step of subjecting the tissue to a mixture of water and a liquid dehydrating agent consisting essentially of a blend of between about 30 and 45 percent by volume of methyl alcohol and between 70 and 55 percent by volume of isopropyl alcohol, the total constituting 100 percent, staining the hydrated tissue, and then dehydrating the stained tissue by subjecting it to the same dehydrating agent.

6. The method of claim 5 of hydrating histological or cytological tissue comprising the step of subjecting the tissue to a mixture of water and a liquid dehydrating agent consisting essentially of a blend of between about 30 and 45 percent by volume of methyl alcohol and between about 70 and 55 percent by volume of isopropyl alcohol, the total constituting 100 percent, repeating the step with successively increasing amounts of water, staining the hydrated tissue, and then dehydrating the stained tissue by subjecting it to the same dehydrating agent.

7. The method of hydrating histological or cytological tissue comprising the step of subjecting the tissue to a mixture of water and a liquid dehydrating agent wherein the amount of isopropyl alcohol is about 60 percent by volume and the amount of methyl alcohol is about 40 percent by volume, staining the hydrated tissue, and then dehydrating the stained tissue by subjecting it to the same dehydrating agent.

8. The method of claim 7 of hydrating histological or cytological tissue comprising the step of subjecting the tissue to a mixture of water and a liquid dehydrating agent wherein the amount of isopropyl alcohol is about 60 percent by volume and the amount of methyl alcohol is about 40 percent by volume, repeating the step with successively increasing amounts of water, staining the hydrated tissue, and then dehydrating the stained tissue by subjecting it to the same dehydrating agent.

* * * * *

UNITED STATES PATENT AND TRADEMARK OFFICE
CERTIFICATE OF CORRECTION

PATENT NO. : 4,911,915

DATED : Mar. 27, 1990

INVENTOR(S) : Jerry L. Fredenburgh

It is certified that error appears in the above-identified patent and that said Letters Patent is hereby corrected as shown below:

Column 1, line 55; "in" should read -- is --.

Column 2, line 63; "water but" should read -- water, but --.

Column 2, line 67; "of" (first occurrence) should read -- or --.

Column 3, line 7; "advantageous but" should read
  -- advantageous, but --.

Column 4, line 58; "to its" should read -- thereto --.

Column 5, line 4; "being" should read -- begin --.

Column 8, line 1; "uses" should read -- used --.

Column 8, line 65; "staining. has" should read
  -- staining. Agent X has --.

Signed and Sealed this

Ninth Day of July, 1991

Attest:

HARRY F. MANBECK, JR.

Attesting Officer

Commissioner of Patents and Trademarks